United States Patent [19]

Doelle

[11] Patent Number: 4,797,360

[45] Date of Patent: Jan. 10, 1989

[54] CONVERSION OF SUCROSE TO FRUCTOSE AND ETHANOL

[75] Inventor: Horst W. Doelle, Kenmore, Australia

[73] Assignee: The University of Queensland, Australia

[21] Appl. No.: 936,764

[22] Filed: Dec. 2, 1986

Related U.S. Application Data

[63] Continuation of Ser. No. 594,580, Mar. 29, 1984, abandoned.

[30] Foreign Application Priority Data

Sep. 27, 1983 [AU] Australia .............................. PG1587

[51] Int. Cl.$^4$ .......................... C12P 19/02; C12P 7/06; C12P 7/14; C12N 1/20
[52] U.S. Cl. .................................. 435/105; 435/161; 435/162; 435/822
[58] Field of Search ............... 435/105, 822, 161, 162, 435/253

[56] References Cited

U.S. PATENT DOCUMENTS

| | | | |
|---|---|---|---|
| 4,317,880 | 3/1982 | Heady | 435/94 |
| 4,326,036 | 4/1982 | Hayes | 435/161 |
| 4,335,207 | 6/1982 | Heady | 435/94 |
| 4,350,765 | 9/1982 | Chibata et al. | 435/161 |
| 4,356,262 | 10/1982 | Heady | 435/105 |
| 4,403,034 | 9/1983 | Rogers et al. | 435/161 |
| 4,413,058 | 11/1983 | Arcuri et al. | 435/161 |
| 4,443,543 | 4/1984 | Rogers et al. | 435/161 |
| 4,443,544 | 4/1984 | Rogers et al. | 435/162 |
| 4,517,298 | 5/1985 | Tedder | 435/160 |

OTHER PUBLICATIONS

Dedonder, "Levansucrase of *Bacillus subtilis*", (1966), *Methods in Enzymology*, vol. VIII, pp. 500–505.
E. Lyness et al., "Ethanol Production from Cane Juice by *Zymomonas mobilis*", Biotechnology Letters, vol. 3, No. 5, 1981, pp. 257–260.
Sue Cromie et al., "Nutritional Effects on the Kinetics of Ethanol Production from Glucose by *Zymomonas mobilis*", European J. Appl. Microbiol Biotechnol, vol. 11, 1981, pp. 116–119.
P. L. Rogers et al., "Ethanol Production by *Zymomonas mobilis*", Advances in Biochemical Engineery and Biotechnology, vol. 23, 1982, pp. 37–84.
E. Lyness et al., "Effect of Temperature on Sucrose to Ethanol Conversion by *Zymomonas mobilis* Strains".
Ed Lyness et al., "Fermentation Pattern of Sucrose of Ethanol Conversions by *Zymomonas mobilis*", Biotechnology and Bioengineering, vol. 23, 1981, pp. 1449–1460.
N. Stevnsborg et al., "Performance Assessment of Two Patent Strains of *Zymomonas mobilis* in Batch and Continuous Fermentations".
E. A. Dawes, et al., *Biochem. J.*, "Sucrose Utilization by *Zymomonas mobilis*: Formation of a Levan", (1966), vol. 98, pp. 804–812.
Yong K. Park, et al., *Biotechnology Letters*, "Study of Levan Formation During Fermentation of *Zymomonas mobilis* on Sucrose", (1983), vol. 5, No. 8, pp. 515–518.
K. J. Lee, *Biotechnology Letters*, "The Kinetics of Ethanol Production by *Zymomonas mobilis* on Fructose and Sucrose Media", (1981), vol. 3, No. 5, pp. 207–212.

*Primary Examiner*—Charles F. Warren
*Assistant Examiner*—Elizabeth A. Hanley
*Attorney, Agent, or Firm*—Foley & Lardner, Schwartz, Jeffery, Schwaab, Mack, Blumenthal & Evans

[57] ABSTRACT

The conversion of sucrose of fructose and ethanol by fermentation using the microorganism "Zymomonas mobilis" and/or the enzyme immobilised levansucrase can be effected at sucrose concentrations greater than 30% where the fermentation is effected at microorganism and/or concentrations 0.01% to 0.5% (by weight) in a fermentation medium with a pH in the range of 4.0 to 7.0 and a temperature range of 35° C. to 40° C.

17 Claims, No Drawings

CONVERSION OF SUCROSE TO FRUCTOSE AND ETHANOL

This is a continuation of application Ser. No. 594,580, filed Mar. 29, 1984, now abandoned.

BACKGROUND OF THE INVENTION

1. Field of the Invention

This invention relates to a method for converting sucrose to fructose and ethanol.

2. Prior Art

The sugar industry has become concerned following recent announcements by many major food and drink manufacturing companies that they intend replacing sugar with fructose obtained from corn syrup as a sweetener. Fructose is nearly twice as sweet as sugar and so only half the amount is required for the same level of sweetness. In addition, the calorific value of fructose is lower than that of sucrose which is important in this health-conscious world.

The conversion of corn syrup to fructose is energy dependent as the corn syrup must first be converted to glucose. With the process presently in use, the yield of fructose is low and the production of slime in the fermenter is a problem.

The production of ethanol from sugar cane is well known and in Brazil, the ethanol is mixed with petrol to produce "gasahol". This process is only economic in countries which have large areas available for the cultivation of sugar cane and where local oil reserves are low, requiring the importation of oil, with the resultant drain on foreign reserves.

SUMMARY OF THE PRESENT INVENTION

It is an object of the present invention to provide a method for producing fructose and ethanol from sucrose on an economic basis.

It is a preferred object to provide such a method where the energy input is low.

It is a further preferred object to provide a method where the purity of the sucrose is not vital to the success of the method.

It is a still further preferred object to provide a method where the ethanol produced can be used as a energy source to maintain the method in train, and where the production of slime in the fermenter is eliminated, or at least minimised.

Other preferred objects of the present invention will become apparent from the following description.

In one aspect the present invention resides in a method for the production of fructose and ethanol from sucrose, including the step of fermenting sucrose, as the fermentation substrate, using the microorganism *Zymomonas mobilis* and the enzyme immobilised levansucrase as the fermentation agent in the presence of a fermentation medium wherein the concentration of the sucrose is greater than 30%.

(The concentration is calculated by weight, where 1% equals 10 grams/liter).

One strain of the microorganism "Zymomonas mobilis has been deposited in the culture collection of the University of Queensland, Microbiology Department, St. Lucia, Queensland, Australia, under Deposit No. UQM2716, and in the American Type Culture Collection (ATCC), 12301 Parklawn Drive, Rockville, Md. 20852, U.S.A. on the under Deposit No. 39676

The enzyme immobilised levansucrase is identified by Deposit No. EC2.4.1.10 of the Enzyme Nomenclature Committee of the International Union of Biochemists.

Preferably the sucrose is obtained from sugar cane or sugar beet and may be supplied to the fermenter in the form of refined sugar, crushed sugar cane juice, molasses or the like.

Preferably the sucrose concentration is the range of 35–50%, with a concentration of approximately 40% being most preferred for maximum fructose yield.

Preferably the fermentation medium includes any one or more of the following components: peptone, yeast extract, potassium dihydrogen phosphate ($KH_2PO_4$), ammonium sulphate (($NH_4)_2SO_4$), urea, and magnesium sulphate ($MgSO_4 7H_2O$). Preferably the components are provided in the concentration range of 0.01% to 0.5% each, with approximately 0.2% being preferred.

Preferably the microorganism *Zymomonas mobilis* and the enzyme levansucrase are present in the concentration range of 0.01% and 0.5%, with a concentration of approximately 0.2% being especially preferred.

Preferably the pH of the fermentation process is maintained within the range of 4.0 to 7.0, with a pH of approximately 6.0 being preferred.

Preferably the temperature in the fermenter is maintained in the range of 35°–40° C. This temperature range appears to produce the best fructose yield and eliminates, or markedly reduces, the production of slime in the fermenter.

Preferably, when the fermentation has been completed, the microorganism and immobilised levansucrase is separated from the fermentation products (e.g. by centrifuging), the ethanol is distilled off and the fructose is concentrated to produce fructose syrup and/or crystallized fructose.

DETAILED DESCRIPTION OF THE PREFERRED EMBODIMENTS

To enable the invention to be fully understood, preferred examples of the method will now be described.

EXAMPLE I

Crushed sugar cane juice is pumped direct from the sugar mill crushes to the fermenter to provide a sucrose concentration of 42%.

If required, the fermentation medium containing any one or more of peptone, yeast extract, potassium dihydrogen sulphate, ammonium sulphate and magnesium sulphate is prepared, with each component having a concentration of 0.21% and added to the fermenter with the microorganism at a concentration of 0.22%.

The pH of the fermenter is adjusted to 5.8 and the temperature raised to 37° C.

The fermentation process is carried out fairly quickly and is completed in approximately 24–50 hours. The fermentation "liquor" is centrifuged or filtered to remove the microorganism before undergoing distillation to recover the ethanol. The fructose produced is then concentrated to form a fructose syrup.

EXAMPLE II

Crushed sugar beet juice is placed in the fermenter at a sucrose concentration of 36%.

The fermentation medium of Example I, at a concentration of 0.15%, is added to the fermenter with the enzyme immobilized levansucrase at a concentration of 0.15%. The pH of the fermenter is adjusted to 6.1 and the temperature raised to 39° C.

The fermentation process is carried out for 24-30 hours until the enzyme has converted the sucrose to fructose and glucose. The microorganism *Zymomonas mobilis* is then added to the fermenter in the concentration of 0.25% and this converts the glucose to ethanol.

The fermentation "liquor" is centrifuged or filtered to remove the microorganism and enzyme and the ethanol is then distilled off. The fructose produced is then concentrated to form a fructose syrup and may then be crystallized.

It has been calculated from experiments carried out that 1 tonne of sucrose will produce approximately 0.5 tonne of fructose, 0.25 tonne of ethanol and 0.25 tonne of carbon dioxide ($CO_2$).

The ethanol produced has commercial value as a component for gasahol or as a base product in the chemical industry e.g. for the production of ethylene, while the other by-product, carbon dioxide, may be used for dry ice or as a carbon source for the growth of algae biomass.

The fermentation process requires only a low energy input as the microorganism produces a fair amount of heat during the fermentation process. In addition, the fermentation is carried out in semianaerobic conditions, avoiding the need for aerating pumps, the fermentation components and products only requiring little mechanical stirring.

Experiments have shown that the success of the fermentation process is not wholly dependent on the quality of the sucrose as the substitute. Successful tests have been carried out even on rotting cane which indicates that the process is particularly suited for industrial application and the fermenter can be provided adjacent a sugar mill to reduce transport costs. As the sucrose does not have to be sterilized, the energy input can be kept low. As little, if any slime is produced in the fermenter, cleaning costs for the fermenter are negligible, assisting the economics of the process. The economics are further improved as the microorganism does not take up the fructose produced by the process.

World production quotas apply on the production of sucrose but not on fructose and so the process provides an additional market for sugar cane.

It would be readily apparent to the skilled addressee that various changes and modifications may be made to the Examples described without departing from the present invention.

I claim:

1. A method for the production of fructose and ethanol from sucrose, comprising the step of fermenting sucrose, using the microorganism *Zymomonas mobilis* in the presence of a fermentation medium wherein the concentration of sucrose is greater than 30% by weight, to produce a fermentation product consisting essentially of ethanol and fructose under semi-anaerobic conditions.

2. A method as claimed in claim 1, wherein the sucrose concentration is in the range of 30% to 50% by weight.

3. A method as claimed in claim 2, wherein the sucrose concentration is approximately 40% by weight.

4. A method as claimed in claim 1, wherein the fermentation medium comprises at least one component selected from the group consisting of peptone, yeast extract, potassium dihydrogen phosphate, ammonium sulphate, urea and magnesium sulphate, the concentration of the component in the fermentation medium being in the range of 0.01% to 0.5% by weight.

5. A method as claimed in claim 4, wherein the concentration of the component in the fermentation medium is approximately 0.2% by weight.

6. A method as claimed in claim 1, wherein the concentration of the microorganism *Zymomonas mobilis* in the fermentation medium is in the range of 0.01% to 0.5% by weight.

7. A method as claimed in claim 6, wherein the concentration of the microorganism *Zymomonas mobilis* is approximately 0.2% by weight.

8. A method as claimed in claim 1, wherein the fermentation process is maintained at a pH level in the range of 4.0 to 7.0.

9. A method as claimed in claim 8, wherein the pH level is maintained at approximately 6.0.

10. A method as claimed in claim 1, wherein the fermentation process is maintained at a temperature in the range of 35° C. to 40° C.

11. A method as claimed in claim 1, further comprising, at the completion of the fermenting of sucrose, the steps of (i) separating the microorganism *Zymomonas mobilis* from a fermentation product consisting essentially of fructose and ethanol; and then (ii) removing ethanol from the fermentation product to concentrate said fructose.

12. A method as claimed in claim 1, wherein the fermentation medium comprises the enzyme levansucrase.

13. A method as claimed in claim 12, wherein the step of fermenting sucrose comprises using the levansucrase to convert the sucrose to fructose and glucose and then adding the microorganism *Zymomonas mobilis* to the fermentation medium to convert the glucose to ethanol.

14. A method as claimed in claim 1, wherein the microorganism *Zymomonas mobilis* has the characteristics of strain ATCC No. 39676.

15. A method as claimed in claim 1, wherein said fermenting of sucrose is a single-stage fermentation process.

16. A method as claimed in claim 1, wherein production of slime during said fermenting of sucrose is eliminated.

17. A method as claimed in claim 1, wherein the pH of said fermentation medium is adjusted to between about 5.8 and 6.1 for said fermenting of sucrose.

* * * * *